United States Patent [19]

Taylor et al.

[11] Patent Number: 5,347,021

[45] Date of Patent: * Sep. 13, 1994

[54] PROCESS OF VAPOR PHASE CATALYTIC HYDROGENATION OF MALEIC ANHYDRIDE TO GAMMA-BUTYROLACTONE IN HIGH CONVERSION AND HIGH SELECTIVITY USING AN ACTIVATED CATALYST

[75] Inventors: Paul D. Taylor, West Milford; Waldo De Thomas, Parsippany; Donald W. Buchanan, Jr., Wayne, all of N.J.

[73] Assignee: ISP Investments Inc., Wilmington, Del.

[*] Notice: The portion of the term of this patent subsequent to Aug. 20, 2008 has been disclaimed.

[21] Appl. No.: 656,388

[22] Filed: Feb. 19, 1991

Related U.S. Application Data

[63] Continuation-in-part of Ser. No. 521,065, Apr. 16, 1990, abandoned.

[51] Int. Cl.$^5$ .............................................. C07D 307/33
[52] U.S. Cl. ...................................... 549/325; 549/326; 568/885
[58] Field of Search ................. 549/325, 326; 502/342; 568/885

[56] References Cited

U.S. PATENT DOCUMENTS

| | | | |
|---|---|---|---|
| 3,580,930 | 5/1971 | Miya et al. | 549/325 |
| 4,420,622 | 12/1983 | Van de Moesdijk et al. | 549/326 |
| 4,652,685 | 3/1987 | Cawse et al. | 568/864 |

FOREIGN PATENT DOCUMENTS

| | | | |
|---|---|---|---|
| 46-3775 | 1/1971 | Japan | 549/325 |

*Primary Examiner*—C. Warren Ivy
*Assistant Examiner*—Ba K. Trinh
*Attorney, Agent, or Firm*—Walter Katz; Marilyn J. Maue; Joshua J. Ward

[57] ABSTRACT

Vapor phase catalytic hydrogenation of maleic anhydride to gamma-butyrolactone is achieved in a conversion of 95% or more and a selectivity of 80% or more during a prolonged period of production. The process uses an activated catalyst prepared by reducing a catalyst composition comprising 30–65% by weight of CuO, 18–50% by weight of ZnO and 8–22% by weight of $Al_2O_3$, and activating the reduced catalyst composition in hydrogen at an activation temperature of at least 400° C., preferably 400° to 525° C., and optimally about 425° C. The process suitably is carried out under predetermined and advantageous process conditions, including a defined molar ratio of hydrogen to maleic anhydride in the vapor reactant stream, a selected pressure during hydrogenation, a defined feed rate space velocity, a predetermined contact time, and a suitable reaction temperature.

15 Claims, No Drawings

PROCESS OF VAPOR PHASE CATALYTIC HYDROGENATION OF MALEIC ANHYDRIDE TO GAMMA-BUTYROLACTONE IN HIGH CONVERSION AND HIGH SELECTIVITY USING AN ACTIVATED CATALYST

CROSS-REFERENCE TO RELATED PATENT APPLICATIONS

This application is a continuation-in-part of U.S. patent application Ser. No. 521,065, filed Apr. 16, 1990, by the same inventors and assigned to the same assignee as herein now abandoned.

This application is related to U.S. patent application Ser. No. 509,431, filed Apr. 16, 1990, now U.S. Pat. No. 5,041,564, assigned to the same assignee as herein, which disclosure is incorporated by reference.

BACKGROUND OF THE INVENTION

1. Field of the Invention

This invention relates to a process of vapor phase catalytic hydrogenation of maleic anhydride to gamma-butyrolactone, and, more particularly to such process which is carried out using an activated catalyst, and under predetermined reaction conditions, which enables a substantially quantitative conversion and high selectivity to gamma-butyrolactone during a prolonged period of production.

2. Description of the Prior Art

Vapor phase catalytic hydrogenation of maleic anhydride to gamma-butyrolactone (hereinafter referred to as "butyrolactone") is an old and well established art for which a great many processes and conditions have been tried. However, commercial practice in respect to the production of butyrolactone from maleic anhydride has not been entirely successful, especially in terms of high conversion and high selectivity to butyrolactone. These deficiencies usually occur because of low catalytic activity and/or less than optimum process conditions.

Dunlop, in U.S. Pat. No. 3,065,243, for example, described a process in which a feed compound, such as maleic anhydride, succinic anhydride, or an acid or ester thereof, was vaporized and the vapors in hydrogen passed over a reduced copper-chromite catalyst. However, conversion and selectivity to butyrolactone was relatively low.

Kyowa, in U.K. Patent No. 1,168,220 disclosed that a reduced copper-zinc catalyst could be used in place of copper-chromite but with only marginally improved results.

Miller, in U.S. Pat. No. 4,001,282, described a similar vapor process carried out in the presence of water. The catalysts used were reduced copper-chromite, copper-zinc, and copper-zinc-chrome catalysts. Water, however, increased the complexity of the process and, accordingly, the process did not attain commercial success.

De Thomas, in U.S. Pat. No. 4,105,674, used relatively expensive copper-palladium or copper-platinum catalysts to carry out the hydrogenation.

Miya, in U.S. Pat. No. 3,580,930, utilized a copper-zinc-chromium catalyst in an attempt to minimize the formation of by-products. Low yields of butyrolactone were obtained, however, with this catalyst.

Attig, in EPA 332,140, published 6/28/89, described vapor phase hydrogenation of maleic anhydride to tetrahydrofuran and butyrolactone using a catalyst comprising copper-zinc-chromium-alumina. Selectivity to butyrolactone, however, was only 50% or less.

In commercial operation according to these and other processes, however, the catalysts and process conditions employed have been found to be less than satisfactory, usually because the catalyst was deactivated through tar and coke formation within a relatively short time. The short life of these catalysts has made it virtually impossible to carry on a production run for a prolonged period of time. The catalysts inevitably had to be regenerated, if at all possible, within a very short period, and fresh catalyst soon introduced into the system. Such procedures required time-consuming shut down times which increased the overall cost of the process.

Accordingly, it is an object of the present invention to provide a process for effecting vapor phase catalytic hydrogenation of maleic anhydride to butyrolactone in high conversion and selectivity during a prolonged production run without requiring fresh catalyst to be introduced into the system.

Another object herein is to provide such a vapor process which provides butyrolactone in a conversion of feed material of 95% or more, preferably 100%, and in a selectivity of 80% or more, preferably 90-95%, or more, during production runs of at least about 2000 hours.

Another object of this invention is to provide an activated catalyst for achieving substantially quantitative conversion and high selectivity to butyrolactone.

Still another object of this invention is to provide such a process which employs an activated catalyst therefor, and process conditions for carrying out the hydrogenation effectively, including a defined ratio of hydrogen to feed compound in the vapor mixture, a predetermined contact time, and a selected feed rate, under which conditions high conversion and selectivity of maleic anhydride to butyrolactone can be achieved by a vapor process.

DEFINITIONS

"Activated Catalyst" is defined herein as a catalyst for hydrogenation of feed compound to butyrolactone having a defined catalyst composition and predetermined physical properties, which is prepared by reducing the catalyst composition, and then activating the reduced catalyst composition under prescribed activation conditions.

"Conversion" is defined herein as the percentage of feed compound consumed in the reaction.

"Selectivity" is defined herein as the percentage of butyrolactone produced as compared to the total amount of starting material consumed.

"Yield" of butyrolactone is defined as the product of conversion times selectivity.

"Feed Compound" is defined as maleic anhydride, succinic anhydride, maleic acid, succinic acid, or esters thereof, or mixture of the foregoing, which can be catalytically converted to butyrolactone by a vapor process.

"Other Product" is defined herein as including the compounds tetrahydrofuran, butanol and propanol, which are obtained in minor amounts herein.

"Contact Time" is defined herein as the time in seconds that the reactants are present in the catalyst zone, and is calculated by dividing the volume of the catalyst in the reactor by the volume of flow of the reactants per second under reactor conditions.

"Feed Rate" or "Space Velocity, LHSV" in hours$^{-1}$, is defined herein as the volume of liquid feed compound per hour per volume of catalyst used in the reactor.

"Feed Composition" is defined herein as the molar ratio of hydrogen to the feed compound in the vapor mixture.

"Percentages" are given by weight of the component in the composition.

SUMMARY OF THE INVENTION

An activated catalyst for vapor phase catalytic hydrogenation of a feed compound selected from maleic anhydride, succinic anhydride, maleic acid, succinic acid, and mixtures thereof, to gamma-butyrolactone, in a conversion of about 95% or more, and a selectivity of about 80% or more, is provided herein. The activated catalyst is capable of production of gamma-butyrolactone for at least 100 hours before reactivation of the catalyst, and for at least 2000 hours without requiring fresh catalyst, and is prepared by:

(a) providing a catalyst composition consisting essentially of about 30-65% by weight of CuO, preferably about 50-60%, about 18-50% by weight of ZnO, preferably about 20-25%, about 8-22% by weight of $Al_2O_3$, preferably about 15-20%, and about 0-5% by weight of a processing aid, preferably about 1-4% graphite, having a total pore volume of about 0.05 to 0.5 cc/g, preferably about 0.1 to 0.4 cc/g, and a surface area of about 20 to 120 $m^2/g$, preferably about 40 to 100 $m^2/g$, (b) reducing said catalyst composition with hydrogen in a gradually increasing hydrogen concentration of from about 0.5% to about 10% initial concentration of hydrogen in an inert diluent to 100% hydrogen in the final concentration under conditions of an increasing reduction temperature of about 150° to about 350° C. for about 5 to 20 hours, and (c) activating the reduced catalyst in hydrogen at an activation temperature of at least 400° C., preferably about 400° to 525° C., most preferably about 425° to 450° C., for a period of at least 8 hours, to provide an activated catalyst having a total pore volume of about 0.08 to 0.3 cc/g, preferably about 0.1 to 0.25 cc/g, and a surface area of about 15 to 100 $m^2/g$, preferably about 30 to 65 $m^2/g$.

The hydrogenation process is carried out under predetermined, advantageous process conditions in which (1) a vapor mixture of the feed compound in hydrogen is provided at a molar ratio of hydrogen to feed compound of about 200:1 to 500:1; and (2) the vapor mixture is passed over the activated catalyst at (a) a pressure of about 50 to 500 psig, and (b) a feed rate space velocity of about 0.03 to 1.0 hours$^{-1}$, for (c) a contact time of less than about 10 seconds, at (d) a reaction temperature of about 200° to about 400° C.

DETAILED DESCRIPTION OF THE PROCESS OF THE INVENTION

A. PREPARATION OF ACTIVATED CATALYST OF INVENTION

1. Preparation of Suitable Catalyst Composition

The catalyst composition of the invention consists essentially of Cu, Zn and Al, in the form of their oxides, in the amounts of about 30-65% by weight of CuO, preferably 50-60%, about 18-50% by weight of ZnO, preferably about 20-25%, and about 8-22% by weight $Al_2O_3$, preferably about 15-20%. The composition also may include, if desired, about 1-5% by weight of the composition of a processing aid such as graphite. A most preferred composition contains about 55% CuO, 23% ZnO, 18% $Al_2O_3$ and 4% graphite.

The catalyst composition may be prepared conveniently by decomposing the corresponding carbonates or nitrates to the oxides at an elevated temperature, generally about 250° to 450° C. The metal carbonates, in turn, can be obtained easily by precipitation of the carbonate compounds from an aqueous reaction mixture of the metal nitrates and a suitable quantity of an alkali metal carbonate. Upon filtering, drying and calcining the carbonates, the oxides are provided in the desired amounts of the composition.

In addition to the compositional requirements for the catalyst of the invention, it is desirable that the catalyst composition possess certain physical properties which enhances its performance in the process. Accordingly, it is preferred that the catalyst composition possess a total pore volume of about 0.05 to 0.5 cc/g, preferably about 0.1 to 0.4 cc/g, and a surface area of about 20 to 120 $m^2/g$, preferably about 40 to 100 $m^2/g$.

2. Reduction of Catalyst Composition

In this step, the catalyst composition is reduced by the conventional method of heating hydrogen at low temperatures to provide a reduced form of the composition. Accordingly, this step is carried out suitably at a reduction temperature of about 170°-300° C., under an inert atmosphere, e.g. that of nitrogen, to which hydrogen is slowly added at a rate such as to avoid a build-up of temperatures above 300° C. within the catalyst bed. The gas flowing over the catalyst bed then is gradually enriched with hydrogen as the temperature is slowly raised.

3. Activation of Reduced catalyst

In accordance with the present invention, the reduced catalyst is subjected to an activation step which enables the activated catalyst to provide desired high conversion and high selectivity during prolonged use in the process without requiring excessive reactivations or substitution of fresh, activated catalyst. The activation step is accomplished by heating the reduced catalyst in hydrogen at a temperature of at least 400° C., preferably at about 400°-525° C., and most preferably, at 425°-450° C. The activation heat treatment effects at least a change in the physical properties of the catalyst which favorably impacts upon conversion, selectivity, and durability of the thus-activated catalyst during production of gamma-butyrolactone over a period of several thousand hours of continuous operation of the process. In particular, it is observed that activation effects a reduction of the total pore volume of the activated catalyst to about 0.08 to 0.3 cc/g, preferably about 0.1 to 0.25 cc/g, and the surface area to about 25 to 100 $m^2/g$, preferably about 30 to 65 $m^2/g$.

B. FORMATION OF VAPOR MIXTURE OF FEED COMPOUND IN HYDROGEN

1. Method of Formation

Vaporization of maleic anhydride into hydrogen to form the vapor mixture may be carried out in the manner described in the reference patents. However, it is preferred that the vapor mixture of the feed compound in hydrogen is obtained by the technique of the above-referred to copending U.S. patent application. In that method, finely divided droplets of the feed compound are formed in a reactor by passing the compound through a spray nozzle and vaporizing the droplets rapidly with hot, recycle hydrogen gas introduced into the reactor and directed at the droplets. Accordingly, a source of the feed compound, such as molten maleic anhydride at about 80° C., is pumped at a suitable pressure and flow rate into a vaporizer vessel through a spray nozzle which converts the mass of molten liquid into fine droplets within the interior of the vessel. A hot, recycle hydrogen gas stream then is introduced into the vessel at a temperature of about 160° to 300° C. The hot, recycle hydrogen gas immediately vaporizes the droplets, that is, before they can reach the walls of the vessel where they could coalesce into a liquid stream, and before they can polymerize and cause fouling of the vaporization process.

2. Molar Ratio of Hydrogen to Feed Compound in Vapor Mixture

This ratio suitably is maintained in the range of about 200:1 to 500:1, and, preferably 230:1 to 280:1. Within this vapor ratio, the process can provide a conversion of 100% and a selectivity of from 85% to 95%. Lower $H_2$/feed compound vapor mixture ratios, e.g. 100:1, on the other hand, result in severe deterioration of selectivity, e.g. to 82% or lower. These lower selectivity ratios also are consistent with an observed catalyst deactivation after less than 100 hours of operation.

C. OTHER PROCESS PARAMETERS

1. Contact Time

The contact time of the reactants with the activated catalyst of the invention suitably is less than about 10 seconds, preferably about 2.0 to 3.5 seconds, and, most preferably, about 2.5–3.0 seconds. In this contain time range, the process will provide a conversion of about 100% and a selectivity of 85–95%. Shorter contact times than the suitable range will favor increased selectivity, however, at the expense of substantially decreased conversion, to below 80%.

2. Pressure during Hydrogenation Reaction

The catalytic hydrogenation process of the invention is carried out at low pressures, suitably in the range of about 50 to 500 psig, and, preferably, about 75 to 250 psig.

3. Feed Rate, or Space Velocity, LHSV (in hours$^{-1}$)

The feed rate of the liquid feed compound over a given amount of catalyst in the process suitably is about 0.03 to 1.0 hours$^{-1}$, preferably, about 0.05 to 0.25 hours$^{-1}$, and, most preferably, about 0.07–0.15 hours$^{-1}$.

D. RESULTS

1. Conversion Percentages

The conversion of feed compound consumed during the reaction is substantially 100%.

2. Selectivity to Butyrolactone

The process of the invention produces several compounds, predominately butyrolactone. Other compounds such as tetrahydrofuran, butanol and propanol, also are produced, however, only in small amounts. In the present process, selectivity with respect to the production of butyrolactone is greater than 80%, and usually about 90–95%.

3. Lifetime of Catalyst

The activated catalyst of the invention can achieve the results described herein over a production period of 2000 hours or more. Usually the activated catalyst is reactivated after the first 100 hours, and then again after about 500 hours. Reactivation is carried out by heating the catalyst in situ in hydrogen at the activation temperature, preferably at about 425°–450° C. for 8–12 hours.

The activated catalyst of the invention may be used in a number of different forms, sizes and shapes, the choice of which is dependent upon whether or not the process of the present invention is carried out in a fixed bed reactor, or with a fluidized bed reactor, since the catalyst can be adapted to suit either of these purposes. Accordingly, the catalyst may be present in the process as a pellet, ring, sphere, extrudate, etc.

The invention will now be illustrated by the following non-limiting examples.

EXAMPLE 1

A. PREPARATION OF ACTIVATED CATALYST OF INVENTION

1. Preparation of Catalyst Composition

A solution of 372 g of copper nitrate, 170 g of zinc nitrate and 125 g of aluminum nitrate in 1 liter of water was prepared at 50° C. Then a solution prepared from 350 g of sodium carbonate in 1 liter of water at 50° C. was slowly added to the metal nitrate solutions to precipitate the respective catalyst precursors as carbonates. The resultant slurries then were filtered and washed in small portions with 2 liters of water at 50° C. After drying at 120° C. for 2 hours, and calcining at 250° C. for six hours, 200 g of catalyst composition was obtained. Then 3% by weight of graphite was admixed with the calcined product. The resultant composition analyzed 55% CuO, 23% ZnO, 18% $Al_2O_3$ and 4% graphite. The total pore volume was 0.1–0.4 cc/g, and the surface area was 20 to 120 m$^2$/g. The resulting calcined catalyst powders were tableted to ¼ inch diameter pellets.

2. Reduction of Catalyst Composition

The catalyst composition prepared above was reduced by hydrogen in a generally inert atmosphere by slowly adding hydrogen to nitrogen and increasing the reduction temperature from 170° C. to 300° C., according to the sequence shown in Table 1 below. The catalyst then were held at the final temperature until no further formation of any water of reduction was observed, whereupon the reduced catalyst was ready for activation.

TABLE 1

| Reduction of Catalyst Composition with Hydrogen at 170°–300° C. | | | | | |
|---|---|---|---|---|---|
| Temp (°C.) | Press. (psig) | $N_2$ (cc/min) | $H_2$ (cc/min) | $H_2$ (%) | Time (hrs) |
| 170 | 150 | 1000 | 10 | 1 | 0.5 |
| 170 | 150 | 1000 | 20 | 2 | 12 |
| 200 | 150 | 1000 | 40 | 4 | 2 |
| 250 | 150 | 1000 | 80 | 8 | 2 |
| 300 | 150 | 1000 | 160 | 16 | 2 |

3. Activation of Reduced Catalyst

The reduced catalyst then was activated at 425° C. in hydrogen for 12 hours as shown in Table 2 below.

TABLE 2

| Temp (°C.) | Press. (psig) | $N_2$ (cc/min) | $H_2$ (cc/min) | $H_2$ (%) | Time (hrs) |
|---|---|---|---|---|---|
| 425 | 150 | 0 | 1000 | 100 | 12 |

The activated catalyst had a total pore volume of about 0.1 to 0.25 cc/g, and a surface area of about 30 to 65 m$^2$/g, and was ready for use in the process for producing gamma-butyrolactone.

B. VAPOR PHASE CATALYTIC HYDROGENATION

A stainless steel, fixed bed reactor tube having an internal diameter of 1.5 inches and a length of 12 inches was packed with 400 g. of the activated catalyst prepared above. A feed mixture of maleic anhydride in hydrogen at a mole ratio of hydrogen to maleic anhydride of 230:1, and at a space velocity, LHSV, of 0.1 hours$^{-1}$, was obtained by feeding molten maleic anhydride into a hydrogen stream. The vapor mixture was introduced into the reactor at a pressure of 150 psig and an inlet temperature of 245° C. After a catalyst contact time of 2.6 seconds, the products exited the catalyst bed at an outlet temperature of 275° C. The process was run continuously for 100 hours. Conversion was 100% and selectivity was 88% to butyrolactone. Then the catalyst was reactivated in situ at 425° C. in 100% hydrogen for 12 hours and production was continued for an additional 400 hours. Conversion was 100% and selectivity increased to 95%.

EXAMPLE 2

The procedure of Example 1 was followed using the sequence of reduction and activation shown in Table 3 below on the catalyst composition.

TABLE 3

| Temp (°C.) | Press. (psig) | $N_2$ (cc/min) | $H_2$ (cc/min) | $H_2$ (%) | Time (hrs) |
|---|---|---|---|---|---|
| Reduction | | | | | |
| 170 | 75 | 1000 | 10 | 1 | 0.5 |
| 170 | 75 | 1000 | 20 | 2 | 12 |
| 200 | 75 | 1000 | 40 | 4 | 2 |
| 250 | 75 | 1000 | 80 | 8 | 2 |
| 300 | 150 | 1000 | 160 | 16 | 2 |
| Activation | | | | | |
| 425 | 150 | 0 | 1000 | 100 | 12 |

The resulting activated catalyst was used in the hydrogenation process at an inlet temperature of 246° C. and an outlet temperature of 250° C. The space velocity, LHSV, was 0.08. Conversion during the run was 100% and selectivity was 92%.

EXAMPLE 3

Examples 1 and 2 were repeated using activation temperatures of 400° and 475° C. The thus-activated catalyst gave similar results in the hydrogenation process with respect to conversion and selectivity.

EXAMPLE 4

The procedure of Examples 1-3 were repeated using a catalyst composition of 34-37% CuO, 37-47% ZnO, 9-12% Al$_2$O$_3$ and 4% graphite. The activated catalyst provided a conversion of 100% and a selectivity of 85% after 100 hours.

EXAMPLE 5

In this example, the catalytic reactor was a stainless steel, fixed bed reactor tube having an internal diameter of 6 inches and a length of 12 feet. The reactor was packed with 1.23 cubic feet of the activated catalyst of Example 1. A vapor feed mixture of maleic anhydride in hydrogen provided a mole ratio of hydrogen to maleic anhydride of 230:1 and a space velocity of 0.1 hours$^{-1}$. The vapor mixture was introduced into the reactor at a pressure of 140-150 psig. and an inlet temperature of 245°-276° C. After a contact time of 2.5-3.0 seconds in the reactor, the products exited the reactor at an outlet temperature of 273°-313° C. The process was run continuously for 2300 hours without requiring fresh catalyst. During this period, the catalyst was reactivated after 100 hours and four times thereafter. Conversion was 99-100% and selectivity was 86-89% to butyrolactone during the period of production.

COMPARATIVE EXAMPLES

EXAMPLE C-1

The procedure of Example 1 was repeated using an activation temperature of 300° C. Conversion was 98% and selectivity was lowered to 75%.

EXAMPLE C-2

The procedure of Example 1 was repeated using an activation temperature of 275° C. Conversion was 98% and selectivity was reduced to 65%.

EXAMPLE C-3

The procedure of Example 1 was repeated except that a molar ratio of hydrogen to maleic anhydride in the vapor mixture was 100:1, and the feed rate was 0.05 hour$^{-1}$. Conversion was 100% and selectivity decreased to 82%.

EXAMPLE C-4

The procedure of Example 1 was repeated except that the catalyst composition was Catalyst L-2823 (United Catalysts, Inc., Louisville, Ky.) which comprised 42% CuO, 21% ZnO, 33% Al$_2$O$_3$ and 1% graphite. Conversion was 90% and selectivity was 79%. After only 10 hours of operation, the reactor became plugged with succinic anhydride and fresh catalyst was needed to produce more butyrolactone.

While the invention has been described with particular reference to certain embodiments thereof, it will be understood that changes and modifications may be made which are within the skill of the art. Accordingly, it is intended to be limited by the appended claims only, in which:

What is claimed is:

1. A process for vapor phase catalytic hydrogenation of a feed compound selected from maleic anhydride, succinic anhydride, maleic acid, succinic acid, and mixtures thereof, to gamma-butyrolactone, in a conversion of about 95%, or more, and a selectivity of about 80%, or more, which comprises:

(a) providing an activated catalyst composition in a reactor, said catalyst being capable of production of gamma-butyrolactone for at least about 100 hours before reactivation of the catalyst, and for at least about 2000 hours without requiring fresh catalyst, comprising:

(1) said composition consisting essentially of about 30-65% by weight of CuO, about 18-50% by weight of ZnO, about 8-22% by weight of $Al_2O_3$, having a total pore volume of about 0.05 to 0.5 cc/g, and a surface area of about 20 to 120 $m^2/g$, (2) reducing said catalyst composition with hydrogen in a gradually increasing hydrogen concentration of from about 0.5% to about 10% initial concentration of hydrogen in an inert diluent to 100% hydrogen in the final concentration under conditions of an increasing reduction temperature of about 150° to about 350° C. for about 5 to 20 hours, and (3) activating the reduced catalyst in hydrogen at an activation temperature of at least 400° C., for a period of at least about 8 hours, to provide an activated catalyst having a total pore volume of about 0.08 to 0.3 cc/g, and a surface area of about 15 to 100 $m^2/g$, (b) providing a vapor mixture of said feed compound in hydrogen at a molar ratio of hydrogen to feed compound of about 200:1 to 500:1, and (c) passing said vapor mixture over said activated catalyst at (i) a pressure of about 50 to 500 psig, and (ii) a feed rate space velocity of about 0.03 to 1.0 hours$^{-1}$, for (iii) a contact time of less than about 10 seconds, at (iv) a reaction temperature of about 200° to about 400° C., said process being capable of production of gamma-butyrolactone for at least about 100 hours before reactivation of the catalyst, and of at least about 2000 hours without requiring fresh catalyst.

2. A process according to claim 1 wherein, in (b), said molar ratio of hydrogen to feed compound in the vapor mixture is about 230:1 to 280:1.

3. A process according to claim 1 wherein, in (c) (i), the vapor phase catalytic hydrogenation reaction is carried out at a pressure of about 75 to 250 psig.

4. A process according to claim 1 wherein, in (c) (iii), the contact time is about 2.0 to about 3.5 seconds.

5. A process according to claim 4 wherein, in (c) (iii), the contact time is about 2.5-3.0 seconds.

6. A process according to claim 1 wherein, in (c) (iv), the vapor phase catalytic hydrogenation reaction is carried out at a reaction temperature of about 150° to 300° C.

7. A process according to claim 1 wherein the conversion is about 100% and selectivity is about 90-95%.

8. A process according to claim 1 wherein the feed compound is maleic anhydride.

9. A process according to claim 1 wherein the reactor is a fixed bed reactor.

10. A process according to claim 1 wherein, in (b), said vapor mixture is obtained by forming finely divided droplets of said feed compound and contacting said droplets with hot recycle hydrogen gas to vaporize said droplets.

11. A process according to claim 1 wherein, in (a) (3), said activation temperature is 400° to 525° C.

12. A process according to claim 1 wherein, in (a) (3), said activation temperature is 425° to 450° C.

13. A process according to claim 1 wherein, in (a) (1), said catalyst composition consists essentially of about 50-60% by weight of CuO, about 20-25% by weight of ZnO, and about 15-20% by weight of $Al_2O_3$.

14. A process according to claim 1 wherein, in (a) (1), said catalyst composition has a total pore volume of about 0.1 to 0.4 cc/g, and a surface area of about 40 to 100 $m^2/g$, and, in (c), said activated catalyst has a total pore volume of about 0.10 to 0.25 cc/g, and a surface area of about 30 to 65 $m^2/g$.

15. A process according to claim 1 wherein, in (a) (1), said catalyst composition is prepared by calcining the metal carbonates or nitrates to the respective oxides.

* * * * *